United States Patent

Nguyen et al.

[11] Patent Number: 5,908,927
[45] Date of Patent: Jun. 1, 1999

[54] SYNTHESIS OF DEUTERATED OPIATE GLUCURONIDES

[75] Inventors: Hoa Duc Nguyen, Orange; Duc Tien Nguyen, Milpitas; Raymond Albert Schep, Beverly Hills; Trinh Duc Nguyen, Santa Ana; Phuong Thi Ngoc Pham, Orange, all of Calif.

[73] Assignee: High Standard Products Corporation, Inglewood, Calif.

[21] Appl. No.: 08/855,831

[22] Filed: May 12, 1997

Related U.S. Application Data

[60] Provisional application No. 60/018,401, May 22, 1996.
[51] Int. Cl.⁶ .................. C07H 19/01; C07D 489/02
[52] U.S. Cl. .................................. 536/28.1; 546/44
[58] Field of Search ...................... 536/28.1; 546/44

[56] References Cited

U.S. PATENT DOCUMENTS 5,292,899  3/1994  Tius et al. .................. 549/390

FOREIGN PATENT DOCUMENTS 0 324 212 A1  7/1989  European Pat. Off. .
WO 93/05057  3/1993  WIPO .

OTHER PUBLICATIONS

Lawson, J.A. et al.: Synthesis of Morphine–d5 and Codeine–d8. J. heterocyclic Chem. vol. 13, pp. 593–595, Jun. 1976.
Rop et al. J. Chromatogr. B 661:245–253(1994).
Hasselstrom et al. Clin. Pharmacokinet. 24(4):344–354 (1993).
Glare et al. Therapeutic Drug Monitoring 13:226–232 (1991).
Carrupt et al. J. Med. Chem. 34, 1272–1275 (1991).
Yoshimura et al. Tetrahedron Lett. 4, 483–486 (1968).

*Primary Examiner*—Alan L. Rotman
*Assistant Examiner*—Charanjit S. Aulakh

[57] ABSTRACT

A method of synthesizing deuterated morphine-3β-glucuronide, morphine-6β-glucuronide, and codeine-6β-glucuronide is disclosed. The chemicals are used as internal standards for mass spectrometry analyses of morphine, heroin, and codeine uses. They are also useful in the study of metabolism of morphine and codeine.

3 Claims, No Drawings

SYNTHESIS OF DEUTERATED OPIATE GLUCURONIDES

The application claims benefit of USC Provisional Appl. No. 60/018,401 filed May 22, 1996.

FIELD OF THE INVENTION

This invention relates to methods for chemical synthesis of deuterated codeine-6β-glucuronide, morphine-3β-glucuronide, and morphine-6β-glucuronide, to internal standards in diagnostic assays using mass spectrometry to detect codeine, morphine, and heroin uses in biological samples, and to deuterated opiate glucuronides for use in metabolism studies of opiates.

BACKGROUND OF THE INVENTION

Codeine, morphine, and heroin are the three most commonly abused drugs among opiates. Codeine and morphine are natural materials derived from opium while heroin is a synthetic chemical made from acetylation of morphine. In human the main metabolic pathway of these opiates is glucuronidation which occurs in liver microsomes. The major metabolite of codeine is codeine-6β-glucuronide while the major metabolite of morphine and heroin is morphine-3β-glucuronide. Unmetabolized codeine, morphine, and heroin constitute only a very small amount in biological samples. Since morphine-3β-glucuronide is also the major metabolite of heroin, it is apparent that deacetylation of heroin occurs before glucuronidation. In fact the identification of a minor but very characteristic metabolite called 6-monoacetylmorphine has been established as evidence of heroin use. This 6-monoacetylmorphine is the result of the deacetylation of heroin. Another important aspect of morphine and heroin metabolism is the formation of a second glucuronide metabolite, morphine-6β-glucuronide, which, even though usually found in smaller amount compared to morphine-3β-glucuronide, has been shown to be as potent as morphine itself.

Deuterated codeines such as codeine-d3 and codeine-d6 are commercially available and have been used as internal standards for Gas chromatography-Mass spectrometry (GC-MS) analysis of codeine in biological samples. In the process of analysis, deuterated codeine is added in a known amount to samples which are then undergo sample preparation processes before analysis. The use of deuterated codeine as internal standard in GC-MS analysis takes advantage of the fact that any losses of codeine in extraction, derivatization, and transfering processes will also result in similar losses of deuterated codeine. The analysis of codeine using deuterated codeine as internal standard is, therefore, more reliable than the same analysis using codeine analogs as internal standards. Unmetabolized codeine in biological samples are usually in small amount compared to the major metabolite codeine-6β-glucuronide. To increase the sensitivity of GC-MS analysis of codeine, samples usually undergo a hydrolysis step to convert codeine-6β-glucuronide to codeine. This hydrolysis step is very important in GC-MS analysis of opiates and is usually carried out by either acid or base or enzyme. Cares have to be taken in hydrolysis because if the enzyme is not good or if the acid or base is not strong enough, hydrolysis will be incomplete. If the conditions are too harsh, opiates will decompose. Thus if codeine-6β-glucuronide is not completely hydrolysed to codeine, the total codeine concentration in samples will be low and the interpretation of the result can be false negative. It would be desirable to have available deuterated codeine-6β-glucuronides to be used as internal standards for GC-MS analysis of codeine, then the incomplete hydrolysis of codeine-6β-glucuronide will likely result in the same incomplete hydrolysis of deuterated codeine-6β-glucuronide. The GC-MS analysis of codeine using deuterated codeine-6β-glucuronides as internal standards, therefore, would be more reliable than the same analysis using deuterated codeines as internal standards. The availability of deuterated codeine-6β-glucuronides also allows direct analysis of codeine-6β-glucuronide in such techniques that do not require sample hydrolysis as Liquid chromatography-Mass spectrometry (LC-MS). So far the analysis of codeine-6β-glucuronide by LCMS using deuterated codeine-6β-glucuronides has not been reported.

Deuterated morphine such as morphine-d3 is available and is currently used as internal standard for GC-MS analysis of morphine in biological samples of morphine and heroin users. Samples are usually spiked with a known amount of morphine-d3 before subjected to a hydrolysis step to convert all morphine glucuronides (morphine-3β-glucuronide constitutes the highest percentage) and acetylated morphines (very small percentage) to morphine. Again, an incomplete hydrolysis will likely result in lower value for total morphine. Thus it is also desirable to have available deuterated morphine-3β-glucuronides to be used as internal standards for GC-MS analysis of morphine or heroin uses.

Current advances of mass spectrometry already allow analysis of glucuronide conjugates directly. The availability of deuterated codeine-6β-glucuronides and deuterated morphine-3β-glucuronides will allow the direct MS analysis of codeine, morphine, and heroin major metabolites without hydrolysis. The analysis will be simple and the results are more accurate. The analysis can also allow simultaneous determination of unmetabolized codeine, morphine, heroin, and even the characteristic heroin metabolite 6-monoacetylmorphine using the available respective deuterated internal standards.

It has been shown that morphine-6β-glucuronide, the minor metabolite of morphine and heroin in human, is as potent as the parent compound itself The concentration of this metabolite is carefully monitored in subjects given doses of morphine or heroin. Its concentration has been monitored independent of morphine-3β-glucuronide, the inactive metabolite, using High pressure liquid chromatography (HPLC) with either ultraviolet detector or electrochemical detector or fluorometric detector. The current GC-MS analysis method for morphine cannot distinguish between morphine-6β-glucuronide and morphine-3β-glucuronide. The availability of deuterated morphine-6β-glucuronides and deuterated morphine-3β-glucuronides will allow a more sensitive monitoring of both morphine-6β-glucuronide and morphine-3β-glucuronide by methods that do not require sample hydrolysis such as HPLC using MS as detector (usually called LC-MS).

The potency of morphine-6β-glucuronide has led to the manufacture and use of this material as therapeutic drug. The availability of deuterated morphine-6β-glucuronides also allows metabolism studies of this drug even in subjects previously taken medications containing codeine, morphine, or heroin.

The syntheses of codeine-6β-glucuronide, morphine-3β-glucuronide and morphine-6β-glucuronide are documented but there are no known synthesis of deuterated codeine-6β-glucuronide, morphine-3β-glucuronides and morphine-6β-glucuronides. To be useful deuterated opiate glucuronides have to be able to transform to deuterated opiates upon hydrolysis. The generated deuterated opiates have to be stable to all sample preparation processes (hydrolysis, extraction, concentration, derivatization). That also means that none of deuterated opiate glucuronides is converted to undeuterated opiates which will apparently increase the concentration of opiates in the analysis.

OBJECTS OF THE INVENTION

It is the object of the invention to provide processes for chemical synthesis of deuterated codeine-6β-glucuronide, deuterated morphine-3β-glucuronide, and deuterated morphine-6β-glucuronide that are useful as mass spectrometry internal standards for use in assays detecting the use of codeine, morphine, and heroin in biological samples. Another object of the invention is to provide materials for differential mass spectrometry analysis of the active morphine and heroin metabolite, morphine-6β-glucuronide, from the inactive, morphine-3β-glucuronide. Another object of the invention is to provide materials for analysis of codeine, morphine, and heroin metabolites without the need of a hydrolysis step in techniques such as LC-MS. Another object of the invention is to provide materials for the metabolism studies of opiate glucuronides regardless of what medications subjects have taken previously.

SUMMARY OF THE INVENTION

Embodiments of the invention provide methods of producing deuterated opiate glucuronides by reacting deuterated opiates or protected deuterated opiates with a common protected sugar methyl(tri-O-acetyl-β-D-glucopyranosyl bromide)uronate. Other embodiments of the invention provide methods for removing all the protective groups of the coupling products without destroying the deuterated opiate glucuronides.

In other embodiments, the invention provides deuterated opiate glucuronides that are deuterated in the opiate moiety. The deuterated opiate glucuronides are useful as internal standards in assays detecting opiate uses by mass spectrometry. They are also useful for metabolism studies of opiate glucuronides.

DETAILS DESCRIPTION OF THE PREFERRED EMBODIMENT

As used herein the following terms have the meaning as indicated:

"Deuterated" codeine means codeine that are labelled with at least one deuterium atom. The deuterium atoms are chemically bonded to at least one carbon atom. A representative example is provided by codeine-d3 wherein three deuterium atoms are chemically bonded to a carbon atom that is bonded to the nitrogen atom in the codeine molecule.

"Deuterated" morphine means mophine that are labelled with at least one deuterium atom. The deuterium atoms are chemically bonded to at least one carbon atom. A representative example is provided by morphine-d3 wherein three deuterium atoms are chemically bonded to a carbon atom that is bonded to the nitrogen atom in the mophine molecule.

"Deuterated codeine-6β-glucuronide" means deuterated codeine-6-β-glucuronide synthesized from the above deuterated codeine. A representative example is provided by codeine-6-β-glucuronide-d3.

"Deuterated morphine-3β-glucuronide" means deuterated morphine-3-β-glucuronide synthesized from the above deuterated morphine. A representative example is provided by morphine-3-β-glucuronide-d3.

"Deuterated morphine-6β-glucuronide" means deuterated morphine-6-β-glucuronide synthesized from the above deuterated morphine. A representative example is provided by morphine-6-β-glucuronide-d3.

"Deuterated opiate" or "Deuterated protected opiate" means deuterated codeines or morphines or protected morphines of the general formulas:

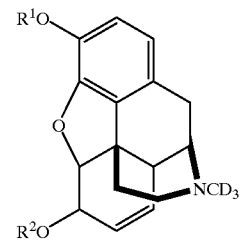

wherein $R^1$ comprises either a hydrogen atom, a methyl or a deuterated methyl group, or an acetate protecting group or any ester protecting groups, and $R^2$ comprises a hydrogen atom.

"Deuterated opiate glucuronides" means deuterated morphine-3-β-glucuronide, deuterated morphine-6-β-glucuronide and deuterated codeine-6-β-glucuronide of the general formulas:

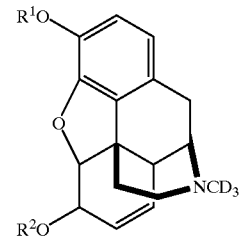

wherein $R^1$ comprises either a hydrogen atom, a methyl or a deuterated methyl group, or a sugar of the structure below, and $R^2$ comprises either a hydrogen atom or a sugar of the structure below.

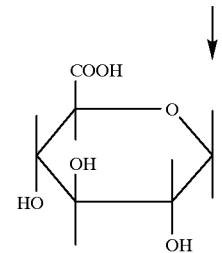

For Codeine-6-β-glucuronide-d3, $R^1$ is a methyl group and $R^2$ is the above sugar group. For Morphine-3-β-glucuronide-d3, $R^1$ is the above sugar group and $R^2$ is the hydrogen atom. For Morphine-6-β-glucuronide-d3, $R^1$ is the hydrogen atom and $R^2$ is the above sugar group.

The common protected sugar methyl(tri-O-acetyl-β-D-glucopyranosyl bromide)uronate is prepared from D-glucurono-6,3-lactone and has the following structure:

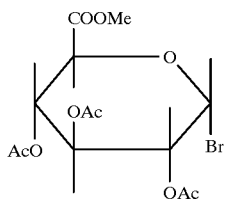

"Biological samples" refer to materials such as blood, serum, plasma, sputum, urine, fecal, hair and mucus samples as well as environmental samples such as soils, clothing, plastic and glass containers and the like.

Embodiments of the invention provide methods of producing deuterated opiate glucuronides of the above general formulas by reacting deuterated opiates or protected deuterated opiates with a common protected sugar methyl(tri-O-acetyl-β-D-glucopyranosyl bromide)uronate followed by removing all the protective groups to produce deuterated opiate glucuronides.

Embodiments of the invention provide a representative method of producing codeine-6-β-glucuronide-d3 of the above formula, as described in examples 1 and 2, by: a) reacting codeine-d3 with the protected sugar methyl(tri-O-acetyl-a-D-glucopyranosyl bromide)uronate, and b) removing the protecting groups of the coupling product to produce codeine-6-β-glucuronide-d3.

Embodiments of the invention also provide a representative method of producing morphin-3β-glucuronide-d3 of the above formula, as described in examples 3, by: a) reacting morphine-d3 with the protected sugar methyl(tri-O-acetyl-a-D-glucopyranosyl bromide)uronate, and b) removing the protecting groups of the coupling product to produce morphin-3β-glucuronide-d3.

Embodiments of the invention also provide a representative method of producing morphin-6β-glucuronide-d3 of the above formula, as described in examples 4,5 and 6, by: a) protecting the phenol group by converting it to an acetate group, and b) reacting morphine-O-acetate-d3 with the protected sugar methyl(tri-O-acetyl-a-D-glucopyranosyl bromide)uronate, and c) removing the protecting groups of the coupling product to produce morphin-6β-glucuronide-d3.

Embodiments of the invention also provide a representative method of analysis of biological samples for morphine-3β-glucuronide by mass spectrometry as described in example 7. A urine sample is made to contain morphine-3β-glucuronide and is spiked with an equal amount of morphine-3β-glucuronide-d3. The sample is then processed by extraction, concentration, and constitution. Upon MS analysis, the concentration of morphine-3β-glucuronide in the sample is quantitated from the relative abundance of the molecular ion of morphine-3β-glucuronide, ion 462, and of morphine-3β-glucuronide-d3, ion 465.

Embodiments of the invention also provide a representative method of analysis of biological samples for morphine-6β-glucuronide by mass spectrometry as described in example 8. A blood sample is made to contain morphine-6β-glucuronide and is spiked with an equal amount of morphine-6β-glucuronide-d3. The sample is then processed by extraction, concentration, and constitution. Upon MS analysis, the concentration of morphine-6β-glucuronide in the sample is quantitated from the relative abundance of the molecular ion of morphine-3β-glucuronide, ion 462, and of morphine-3β-glucuronide-d3, ion 465.

Still other embodiments of the invention provide a representative method of using codeine-6-β-glucuronide-d3 as internal standard for GC-MS analysis of codeine in biological samples as described in example 9. Two urine samples are made to contain codeine-6-β-glucuronide. One sample is spiked with codeine-d3. The other sample is spiked with codeine-6-β-glucuronide-d3 in the amount that would generate the same amount of codeine-d3 as in the former urine sample. Both urine samples are then processed by hydrolysis, extraction, concentration, and reconstitution. Analysis of both processed samples by GC-MS provide the concentrations of codeine which are used to evaluate to efficiency of hydrolysis.

EXAMPLE 1

Synthesis of [3-(triacetyl-2,3,4-b-D-glucopyranoside)-6yl-codeine-d3]uronate

A solution of codeine-d3 (0.18 g, 0.62 mmol), methyl(tri-O-acetyl-β-D-glucopyranosyl bromide)uronate (0.58 g, 1.49 mmol), silver carbonate (0.41 g, 1.49 mmol), and 15 mL benzene was heated at reflux for 4 hrs and cool. The reaction solution was filtered and the filtrate was concentrated. The residue was purified by column chromatography using silica gel as absorbant and eluant chloroform-methanol mixture (ratio 100:1 to 10:1) to give 0.28 g of [3-(triacetyl-2,3,4-β-D-glucopyranoside)-6yl-codeine-d3]uronate as a yellow solid.

EXAMPLE 2

Synthesis of codeine-6-β-glucuronide-d3

A solution of [3-(triacetyl-2,3,4-b-D-glucopyranoside)-6yl-codeine-d3]uronate (0.28 g, 0.45 mmol), lithium carbonate (0.34 g, 4.50 mmol), methanol (4 mL), and water (4 mL) was stirred for 24 hrs then was concentrated. The residue was purified by column chromatography using silica gel as absorbent and eluant chloroform-methanol mixture (ratio 10:1 to 1:1) to give 0.12 g of codeine-6-β-glucuronide-d3 as a yellow solid. Mass spectral analysis shows m/z 479 with an isotopic purity >98%.

EXAMPLE 3

Synthesis of morphine-3-β-glucuronide-d3

Lithium hydroxide hydrate (0.04 g) and methyl(tri-O-acetyl-α-D-glucopyranosyl bromide)uronate (0.42 g, 1.06 mmol) were added to a solution of morphine-d3 (0.10 g, 0.35 mmol) in 2 mL methanol. The resulting solution was stirred for 5 hrs and was treated with 0.10 g lithium carbonate and 2 mL water. The solution was stirred for 16 hrs then concentrated. The residue was purified by column chromatography using silica gel as absorbant and eluant chloroform-methanol mixture (from ratio 10:1 to 1:1) to give 0.07 g morphin-3-β-glucuronide-d3 as white solid. Mass spectral analysis shows m/z 465 with an isotopic purity >98%.

EXAMPLE 4

Synthesis of morphine-3-O-acetate-d3

Morphine-d3 (0.20 g, 0.69 mmol) was dissolved in 4 mL 20% aqueous KHCO3 and was treated dropwise with 1.40 mL acetic anhydride. The resulting solution was stirred for 2 hrs then was extracted with chloroform. The organic phase was dried with MgSO4 and concentrated. The residue was purified by column chromatography using silica gel as absorbant and eluant chloroform-methanol mixture (ratio of 100:1 to 10:1) to give 0.24 g morphine-3-O-acetate-d3 as an oil.

EXAMPLE 5

Synthesis of [acetyl-3-(triacetyl-2,3,4-b-D-glucopyranoside)-6yl-morphine-d3]uronate A solution of morphine-3-O-acetate-d3 (0.24 g, 0.62 mmol), methyl(tri-O-acetyl-b-D-glucopyranosyl bromide) uronate (0.58 g, 1.49 mmol), silver carbonate (0.41 g, 1.49 mmol), and 15 mL benzene was heated at reflux for 4hrs and cool. The reaction solution was filtered and the filtrate was concentrated. The residue was purified by column chromatography using silica gel as absorbant and eluant chloroform-methanol mixture (ratio 100:1 to 10:1) to give 0.39 g of [acetyl-3-(triacetyl-2,3,4-β-D-glucopyranoside)-6yl-morphine-d3]uronate as a yellow solid.

EXAMPLE 6

Synthesis of morphine-6-β-glucuronide-d3

A solution of [acetyl-3-(triacetyl-2,3,4-b-D-glucopyranoside)-6yl-morphine-d3]uronate (0.39 g, 0.60 mmol), lithium carbonate (0.45 g, 6.02 mmol), methanol (5 mL), and water (5 mL) was stirred for 24 hrs then was concentrated. The residue was purified by column chromatography using silica gel as absorbent and eluant chloroform-methanol mixture (ratio 10:1 to 1:1) to give 0.12 g of morphine-6-β-glucuronide-d3 as a yellow solid. Mass spectral analysis shows m/z 465 with an isotopic purity >98%.

EXAMPLE 7

Mass spectrometry analysis of morphine-3β-glucuronide using morphine-3β-glucuronide-d3 as internal standard To a 5 mL drug-free urine was added 50 μL of a 0.1 mg/mL methanol solution of morphine-3-β-glucuronide to make a urine sample containing 1000 ng/mL morphine-3-β-glucuronide. To this urine solution was then added 50 μL of a 0.1 mg/mL methanol solution of morphine-3-β-glucuronide-d3. The sample is then passed through a C18 Sep Pak cartridge which was conditioned with 2×6 mL methanol followed by 2×6 mL distilled water. The cartridge was then washed with 2×6 mL 5 mM ammonium sulfate followed by 6 mL distilled water. The cartridge was then eluted with 1 mL of 10 mM sodium hydrogen phosphate and acetonitrile (9:1). The eluant was evaporated to dryness under a stream of nitrogen. The residue was reconstituted with 0.5 mL methanol and analyzed by electrospray MS. A 1:1 ratio of peaks 462:465 was observed.

EXAMPLE 8

Mass spectrometry analysis of morphine-6β-glucuronide using morphine-6β-glucuronide-d3 as internal standard To a 1 mL blood plasma was added 50 μL of a 0.1 mg/mL methanol solution of morphine-6-β-glucuronide to make a plasma sample containing 5000 ng/mL morphine-6-β-glucuronide. To this plasma was then added 50 μL of a 0.1 mg/ml methanol solution of morphine-6-β-glucuronide-d3. The sample is then passed through a C18 Sep Pak cartridge which was conditioned with 2×6 mL methanol followed by 2×6 mL distilled water. The cartridge was then washed with 2×6 mL 5 mM ammonium sulfate followed by 6 mL distilled water. The cartridge was then eluted with 1 mL of 10 mM sodium hydrogen phosphate and acetonitrile (9:1). The eluant was evaporated to dryness under a stream of nitrogen. The residue was reconstituted with 0.5 mL methanol and analyzed by electrospray MS. A 1:1 ratio of peaks 462:465 was observed.

EXAMPLE 9

MS analysis of codeine in a biological sample using codeine-6-β-glucuronide-d3 and codeine-d3 as internal standards to determine the completeness of hydrolysis A 10 mL drug-free urine was added 100 μL of a 0.1 mg/mL methanol solution of codeine-6-β-glucuronide to make a urine sample containing 1000 ng/mL codeine-6-β-glucuronide. 5 mL of this urine was treated with 50 μL of a 0.1 mg/mL methanol solution of codeine-6-β-glucuronide-d3.

Another 5 mL of this urine was treated with 83 μL of a 0.1 mg/mL methanol solution of codeine-d3. Both urine samples were then subjected to a hydrolysis condition. After hydrolysis, both samples were neutralized and then passed through C18 Sep Pak cartridges which were previously conditioned with 2×6 mL methanol followed by 2×6 mL distilled water. The cartridges were then washed with 2×6 mL ammonium sulfate followed by 2×6 mL distilled water and 2×6 mL ammonium phosphate. The cartridges were then eluted with 2 mL chloroform-isopropanol (9:1). The eluants were evaporated under a stream of nitrogen. The residues were dissolved in 100 μL methanol and analyzed by GCMS. The ion ratio of 299:302 in urine sample spiked with codeine-d3 was compared with the same ion ratio in the other urine sample to determine the completeness of hydrolysis of the glucuronide conjugates.

CONCLUSION

Thus, there have been disclosed processes for the chemical synthesis of novel deuterated opiate glucuronides. It will be apparent to those skilled in the art that various modifications and changes of an obvious nature may be made, and all such modifications and changes are considered to fall within the scope of the invention, as defined by the appended claim.

What is claimed is:

1. A method of producing deuterated codeine glucuronide and deuterated morphine glucuronides comprising the steps of:

a) reacting a deuterated codeine or a deuterated morphine or a deuterated protected morphine of the formulas:

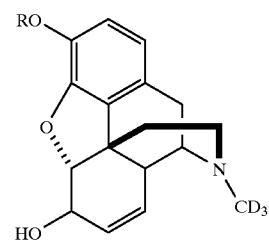

wherein R is either a hydrogen, a methyl group, or an ester protecting group such as an acetyl group, with a protected sugar methyl(tri-O-acetyl-β-D-glucopyranosyl bromide) uronate.

b) removing the protective groups of the coupling products to provide deuterated codeine glucuronide or deuterated morphine glucuronides.

2. A method of producing compounds of claim 1 wherein
a) said deuterated codeine is codeine-d3 and said deuterated morphine is morphine-d3.
b) the resulting deuterated codeine glucuronide is codeine-6-β-glucuronide-d3, and the resulting deuterated morphine glucuronides are morphine-3-β-glucuronide-d3 and morphine-6-β-glucuronide-d3.

3. A method of analysis for the presence and amount of the metabolites of codeine and morphine in a biological sample, comprising adding the compound(s) produced from claim 1 to said sample, processing said sample, and analyzing said sample by mass spectrometry.

* * * * *